United States Patent [19]

Andreiko

[11] Patent Number: 5,254,003

[45] Date of Patent: Oct. 19, 1993

[54] METHOD OF FORMING AND BRACKET OF NICKEL-CHROMIUM-BERYLLIUM BASED ALLOYS

[75] Inventor: Craig A. Andreiko, Alta Loma, Calif.

[73] Assignee: Ormco Corporation, Glendora, Calif.

[21] Appl. No.: 844,794

[22] Filed: Mar. 2, 1992

[51] Int. Cl.$^5$ .............................................. A61C 3/00
[52] U.S. Cl. ...................................... 433/9; 29/160.6
[58] Field of Search ................ 433/8, 9, 24; 29/160.6

[56] References Cited

U.S. PATENT DOCUMENTS

| | | | |
|---|---|---|---|
| 4,592,890 | 6/1986 | Burnett et al. | 433/207 |
| 4,673,354 | 6/1987 | Culler | 433/217.1 |
| 4,978,391 | 12/1990 | Jones | 433/8 |
| 5,011,410 | 4/1991 | Culler et al. | 433/218 |

OTHER PUBLICATIONS

S. A. Aquilino et al., "Tensile Fatigue Limits of Prosthodontic Adhesives", J Dent Res, Mar. 1991, pp. 208–210.
The Critical Role of Rexillium III in Acid-Etched Bridgework, Jeneric Gold Co.
Rexillium III paper on physical properties.

Primary Examiner—John J. Wilson
Attorney, Agent, or Firm—Wood, Herron & Evans

[57] ABSTRACT

A dental bracket is made from an alloy of nickel, beryllium and chromium. The alloy may be that designated by the trademark REXILLIUM III. A groove is disposed in one surface of the bracket to receive an arch wire. An opposite surface of the bracket is roughened to receive an adhesive which has properties of adhering to the bracket and to a patient's tooth. The bracket is formed by heating the alloy to the molten state, pouring the molten alloy into a mold with a cavity in the shape of the bracket and allowing the bracket to cool in air to room temperature. As the bracket cools, the beryllium oxide formed during the heating of the alloy is formed into dendrites. The surface receiving the adhesive is washed with an acid to remove the material in the space between the dendrites and thereby roughen the surface for the reception of the adhesive. The dental bracket is advantageous in that it is made from a single integral piece of material and in that it has properties of preventing tarnishing when scratched. This results from the oxidation of the beryllium oxide during the formation of the bracket and the migration of the beryllium oxide to the surface area where the scratch is located.

13 Claims, 1 Drawing Sheet

METHOD OF FORMING AND BRACKET OF NICKEL-CHROMIUM-BERYLLIUM BASED ALLOYS

This invention relates to a dental bracket and more particularly relates to a dental bracket made from a single integral piece of material with properties of adhering positively to a tooth and of preventing tarnishing when the dental bracket is scratched.

Dental brackets are used to reposition the teeth of a patient so that the cusps in the lower bicuspids will fit into the ridges in the upper bicuspids. Hopefully this repositioning of the patient's teeth will allow the teeth to be retained in good condition for many years in the patient's mouth and will allow the patient's gums to remain in good condition.

The dental brackets now in use are generally formed from more than one (1) member. For example, each bracket generally includes a support member and a pad. The support member is made from a suitable material such as stainless steel and is provided with a groove in one surface to receive an arch wire. The arch wire is disposed in the groove to apply a force to the tooth to move the tooth to the desired position in the patient's mouth. A pad made from a suitable metallic mesh such as a stainless steel mesh is attached to the opposite surface of the support member. An adhesive is disposed in the mesh pad to adhere the mesh pad to the support member and to the patient's tooth.

There are several disadvantages with the brackets now in use. One disadvantage is that the brackets are formed from more than one member. This increases the cost and inconvenience of forming each bracket. Furthermore, the mesh pad is included in the bracket for attachment to the support member and to the patient's tooth. Because of the mesh in the pad, approximately only thirty percent (30%) of the surface area of the bracket is available to receive the adhesive. This limits the locking force which can be applied between the bracket and the patient's tooth to attach the bracket to the tooth.

Bridges are used to position artificial teeth in a patient's mouth fixedly with respect to adjacent teeth in the patient's mouth. In an article entitled "Tensile Fatigue Limits of Prostohodontic Adhesives" prepared by S. A. Aquilino, A. M. Diaz-Arnold and T. J. Piotrowski and published in Vol. 70, No. 3, of the *Journal of Dental Research* in March, 1991, at 2108-210, a material designated by the trademark REXILLIUM III is described for use in such bridges.

This invention provides a bracket formed from a single unitary member. The member is formed at the surface facing the tooth so that substantially all of the area of the bracket is available to be bonded as by adhesive to the tooth. This enhances the bonding force between the bracket and the tooth. The bracket is also advantageous in that it is formed from a material which prevents the bracket from tarnishing in a patient's tooth if the surface of the bracket should inadvertently be scratched.

In one embodiment of the invention, a dental bracket is made from an alloy of nickel, beryllium and chromium. A groove is disposed in one surface of the bracket to receive an arch wire. An opposite surface of the bracket is roughened to receive an adhesive which has properties of adhering to the bracket and to a patient's tooth. The alloy may be that designated by the trademark REXILLIUM III, which is described in detail in the product specification sheet available from the manufacturer, Rx Jeneric Gold Co. of Wallingford, CT, the content of which is hereby expressly incorporated herein by reference. As described in the specification sheet, REXILLIUM III is a non-precious nickel-chromium-beryllium alloy preferably containing about 1.8 weight percent beryllium. Additional properties of REXILLIUM III include:

| Brinell Hardness | 240 |
| --- | --- |
| Proportional Limit | 74,000 psi, 520 kg/mm$^2$ |
| Ultimate Tensile Strength | 155,000 psi, 1090 kg/mm$^2$ |
| Elongation | 9–12% |
| Melting Range | 2250–2350° F., 1232–1238° C. |
| Modulus of Elasticity | 28 × 10$^6$ psi, 198,000 kg/mm$^2$ |
| Specific Gravity | 7.75 gm/cc |

The bracket is formed by heating the alloy to the molten state, pouring the molten alloy into a mold with a cavity in the shape of the bracket and allowing the bracket to cool in air to room temperature. As the bracket cools, the beryllium oxide formed during the heating of the alloy is formed into dendrites. The surface receiving the adhesive is washed with an acid to remove the material in the space between the dendrites and thereby roughen the surface for the reception of the adhesive.

The dental bracket is advantageous in that it is made from a single integral piece of material and that it has properties of preventing tarnishing when scratched. This results from the oxidation of the beryllium oxide during the formation of the bracket and the migration of the beryllium oxide to the surface area where the scratch is located.

Figure 1:
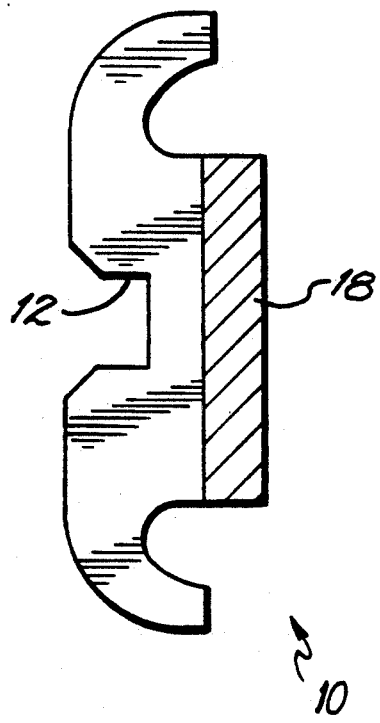
FIG. 1 is a sectional view of a dental bracket constituting one embodiment of the invention.
Figure 2:
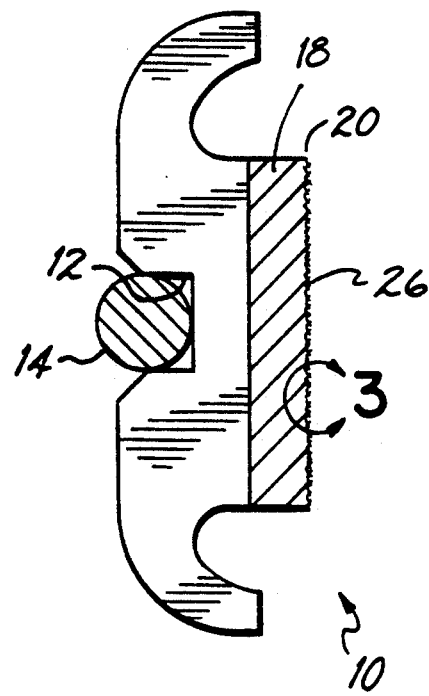
FIG. 2 is a sectional view similar to that shown in FIG. 1 but shows an arch wire in a groove in the bracket.

In one embodiment of the invention, a bracket generally indicated at 10 is made from a nickel-chromium-beryllium alloy. This alloy may be that designated as REXILLIUM III, available from the Rx Jeneric Gold Company of Wallingford, Connecticut, and described in detail hereinabove. As will be seen, the bracket 10 is a unitary member and is provided with a groove 12 for receiving an arch wire 14. The groove 12 is provided with an individual configuration, such as a width and a depth, dependent upon the force to be imposed on a patient's tooth 16 by the arch wire to reposition the tooth to an optimal position in a patient's mouth.

A surface 18 on the bracket 10 opposite the groove 12 is roughened or pitted as at 20 to receive an adhesive 22 which is bonded to such surface and to a patient's tooth 16. A suitable adhesive may be a 4 META adhesive system, which consists of 5% 4-methacryloxyethyl trimellitate anhydride and 95% polymethylmethacrylate initiated by tri-n-butyl borane. A filled BIS-GMA system with methacrylates and a phosphate ester added to the monomer may also be used. The use of such adhesives with the REXILLIUM III material is described in the articles specified above.

The bracket 10 may be formed by heating the alloy to a suitable temperature such as approximately 2400° F. to provide the alloy in a molten state. The molten alloy is then poured into a mold having a cavity with the shape of the bracket 10. The alloy is then allowed to cool in air to room temperature and the bracket may then be removed from the mold. By such a procedure, the beryllium in the alloy is oxidized to form beryllium oxide in the form of dendrites 26 near the surface of the bracket. The dendrites are strong and hard.

Figure 3:
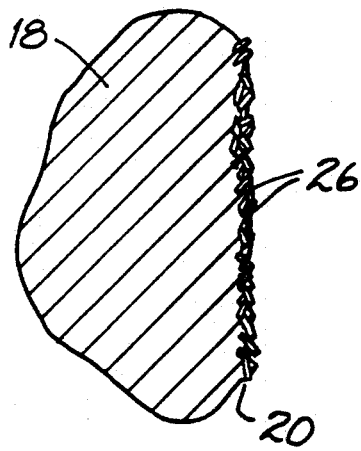
FIG. 3 is a schematic view of a surface of the bracket shown by encircled area 3 shown in FIG. 2, this surface being roughened or pitted to receive an adhesive for attaching this surface to a patient's tooth.
Figure 4:
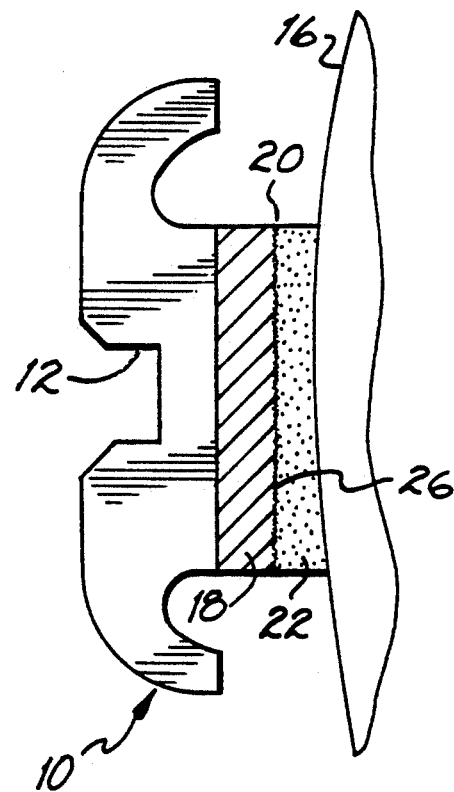
FIG. 4 is a schematic view of the bracket shown in FIGS. 1 and 2 after the attachment of the bracket to the patient's tooth.

The material at the surface 18 between the beryllium oxide dendrites may then be removed as by an acid wash. This removal is facilitated by the fact that the dendrites are under stress so that the acid is able to penetrate into the space between the dendrites and remove the material in this space. This causes the surface 18 to be roughened or pitted as illustrated at 20 in FIG. 3.

Before the acid wash is applied to the bracket 10, the surface 18 to be etched is abraded with particles of aluminum oxide of fifty microns (50u) size at an air pressure of 80 psi. The acid wash may then be obtained by providing (a) a quart of concentrated hydrochloric acid and (b) a quart of hydrochloric acid in methanol. The bracket 10 is initially disposed in solution (b) and then solution (a) is poured into solution (b). The bracket is then retained in this mixture for approximately ten (10) minutes.

The bracket described above has certain important advantages. It provides a unitary integral structure which is hard and strong. The bracket 10 can be positively attached to the patient's tooth 16 because the adhesive 22 covers the entire area of the surface 18. This provides for a strong bond between the bracket and the tooth. In addition to being hard and strong and providing for the roughening of the surface 18, the beryllium oxide is advantageous because it migrates to the surface of the bracket and prevents the surface from tarnishing at any position where the surface of the bracket may be scratched.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. An article for application to a patient's tooth to support an arch wire, comprising:
    a dental bracket made from a nickel-chromium-beryllium based alloy and having a groove at one end for receiving the arch wire, the bracket having a particular surface for bonding to the tooth.

2. The article as set forth in claim 1 wherein the dental bracket is made from an alloy containing up to about 2% beryllium.

3. The article as set forth in either claims 1 or 2 wherein the surface of the bracket includes beryllium.

4. The article set forth in any of claims 1, 2 and 3 wherein dendrite structure is formed when the alloy is cooled from the molten state and wherein the space between the dendrite structure is removed to form the bonding surface.

5. An article for application to a patient's tooth to support an arch wire, comprising:
    a dental bracket made from a nickel-chromium-beryllium based alloy and having a groove on a first surface for receiving the arch wire and having a surface opposite the first surface, and
    an adhesive disposed on the surface of the bracket opposite the first surface with properties of adhering to the bracket and to the patient's tooth.

6. An article as set forth in claim 5 wherein the arch wire is disposed in the groove in the bracket.

7. An article as set forth in claim 5 or 6 wherein the alloy contains up to about 2% beryllium.

8. An article as set forth in claim 5 wherein the surface of the bracket opposite the first surface is roughened before the adhesive is applied to the surface.

9. A method of forming a dental bracket for application to a patient's tooth to support an arch wire, including the steps of:
    heating pellets of a nickel-chromium-alloy to the molten state;
    pouring the molten alloy into a mold having a cavity with the shape of the bracket;
    allowing the alloy to cool, after being poured in the molten state in the mold, to obtain a dendrite structure;
    removing the bracket from the mold; and
    preparing a particular surface of the bracket to remove the material between the dendrites.

10. A method as set forth in claim 9 wherein
    adhesive is applied to the particular surface of the bracket for retention by the particular surface after the particular surface has been prepared, and
    the bracket is adhered by the adhesive to the tooth.

11. A method as set forth in claims 9 or 10 wherein the alloy contains up to about 2% beryllium.

12. A method as set forth in claim 9, wherein
    the bracket is formed with a groove and wherein
    the arch wire is disposed in the groove.

13. A method as set forth in claim 9 wherein the particular surface of the bracket is roughened before the adhesive is applied to the particular surface.

* * * * *